United States Patent [19]

Yamamoto et al.

[11] Patent Number: 4,632,808
[45] Date of Patent: Dec. 30, 1986

[54] CHEMICAL MANIPULATOR

[75] Inventors: Masahiro Yamamoto; Hiroshi Tanaka; Chihiro Watanabe, all of Tokyo, Japan

[73] Assignee: Science and Technology Agency, Tokyo, Japan

[21] Appl. No.: 600,280

[22] Filed: Apr. 13, 1984

[30] Foreign Application Priority Data

Apr. 15, 1983 [JP] Japan .................................. 58-66716
Apr. 21, 1983 [JP] Japan .................................. 58-70419
May 20, 1983 [JP] Japan .................................. 58-88735

[51] Int. Cl.$^4$ ...................... G01N 35/00; G01N 35/02; G01N 37/00
[52] U.S. Cl. ...................................... 422/72; 356/427; 422/63; 422/65; 422/67; 422/100; 494/27; 494/33; 435/291
[58] Field of Search ..................... 422/63–67, 422/72, 73, 100; 435/287, 291; 356/427; 494/33, 27

[56] References Cited

U.S. PATENT DOCUMENTS

| 3,081,158 | 3/1963 | Winter | 422/100 |
| 3,494,201 | 2/1970 | Roach | 422/100 |
| 3,826,622 | 7/1974 | Natelson | 422/65 |
| 3,929,411 | 12/1975 | Takano et al. | 436/180 |
| 4,058,367 | 11/1977 | Gilford | 422/67 |
| 4,208,484 | 6/1980 | Sogi et al. | 422/72 |
| 4,495,149 | 1/1985 | Iwata et al. | 422/100 |

Primary Examiner—Michael S. Marcus
Attorney, Agent, or Firm—Armstrong, Nikaido, Marmelstein & Kubovcik

[57] ABSTRACT

This invention relates to a chemical manipulator adapted to automate analysis of liquids of $\mu l$ unit such as DNA sample. Within the body frame are arranged a sample supply and discharging station, a mixing station, a separating station, and a drying station, each station being provided with a positioning device and a temperature control such as a thermostatic tank if necessary. Reaction containers are accommodated within a bucket which can accommodate a plurality of reaction containers. The bucket is automatically transported between the stations by means of a head element of a manipulator which may be moved in three directions of x, y and z.

2 Claims, 10 Drawing Figures

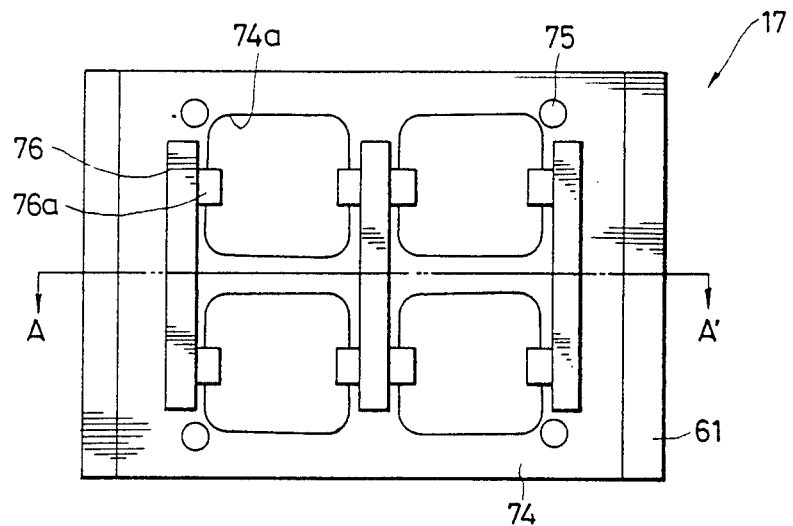
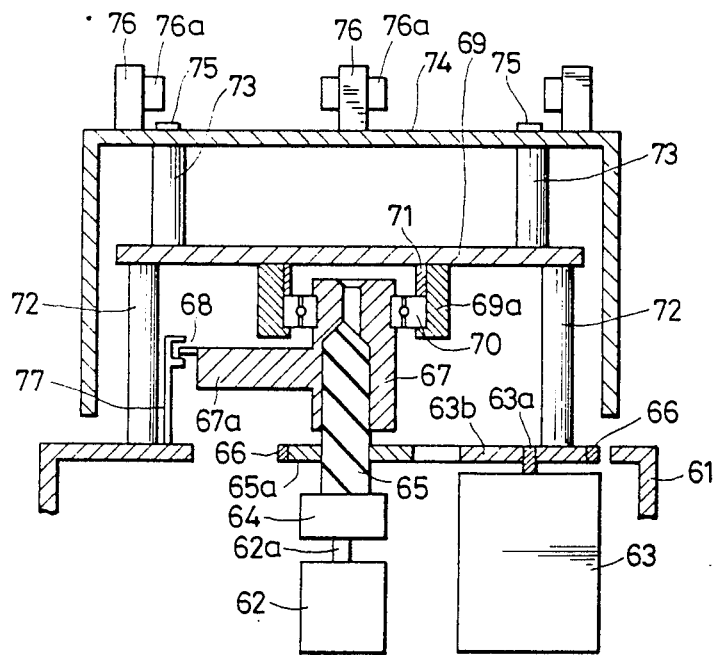

CHEMICAL MANIPULATOR

BACKGROUND OF THE INVENTION

1. Field of the Invention

The present invention relates to a chemical manipulator, and particularly to a new improvement in automation of anaylysis and analyzing process of liquids of $\mu l$ unit of a chemical sample such as DNA sample.

2. Description of the Prior Art

In chemical manipulators of this kind heretofore used, most of complicated procedures have been carried out by manual operation of a research worker. Therefore, where chemicals or radioactive materials which excercise danger over the human body are used, there poses various problems and has disadvantages in that the analyzed results are uneven with individual difference and it takes time.

SUMMARY OF THE INVENTION

It is an object of this invention to provide a manipulator which can automatically process a series of steps of mixing, separating, heating, cooling and the like of a sample in a fine amount of $\mu l$ unit.

It is a further object of the invention to provide a conveying device which can be moved automatically and positively between stations where said series of steps are carried out, respectively.

It is another object of the invention to provide a mixer for a fine amount of sample which is suitable for being incorporated into said series of steps.

To achieve the above-described objects, the apparatus includes, in its body frame, a centrifugal separator capable of accommodating at least more than one reaction containers, a theremostat, a dryer for drying said reaction containers, a reagent supplying device for supplying a reagent to said reaction containers, and a transporting device for moving said reaction containers in a three-dimensional fashion and conveying said containers while being located relative to said centrifugal separator, said thermostat, said dryer and said reagent supplying device, and comprising a controller for automatically controlling said centrifugal separator, said thermostate, said dryer, said reagent supplying device and said transporting device in accordance with an inputted predetermined procedure.

The aforesaid transporting device for moving the reaction container in a three-dimensional fashion to automatically engage and discharge the reaction container comprises a first support shaft rotatably mounted on a movable base, a second support shaft which is provided movably up and down and parallel to said first support shaft in said base, a support plate secured to a lower end of the second support shaft, a pair of rotatable plates rotatably mounted on opposite ends of the support plates and a connecting rod for interconnecting each of the rotatable plates, wherein the first support shaft is provided integral with one rotatable plate, a head element is mounted on the other rotatable plate, the first support shaft is rotated to thereby rotate the head element and the second support shaft is moved up and down to thereby move the head element up and down.

Further, a mixer for a chemical analyzer for mixing a sample and a reagent is designed so that in order to be automatically driven, positioned and rested, a swinging case having a reaction container accommodating portion is swung and driven through an eccentric shaft, and thereafter the rotational position of the eccentric shaft is detected to rest it at a predetermined position thereby enabling the reaction container to be accommodated and removed through the aforesaid automatic transporting device.

BRIEF DESCRIPTION OF THE DRAWINGS

FIG. 1 (b) is a side view of the same;

FIG. 7 is a plan view of a mixer device; and

FIG. 8 is a side sectional view taken on line A-A' of FIG. 7.

DETAILED DESCRIPTION OF THE PREFERRED EMBODIMENTS

Figure 1A:
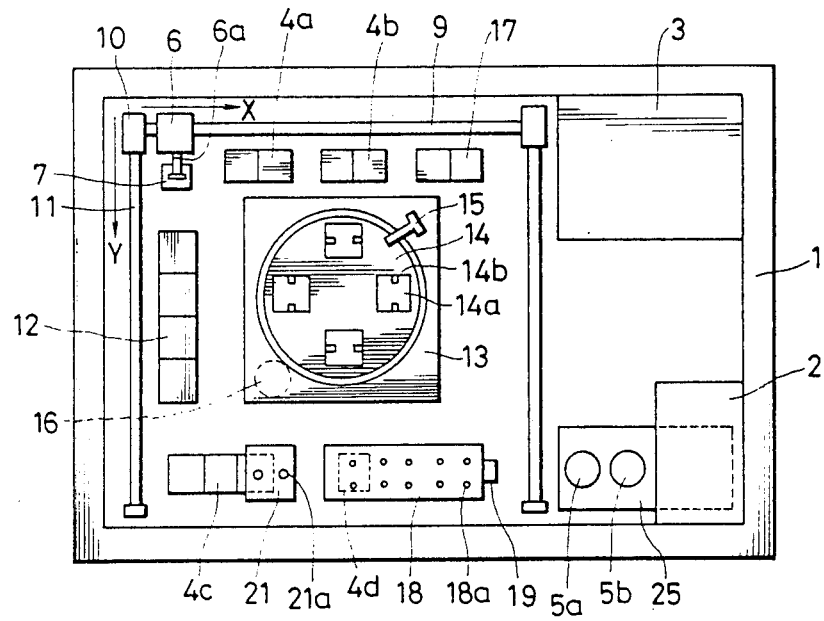
FIG. 1 (a) is a plan view of the whole apparatus.
Figure 1B:
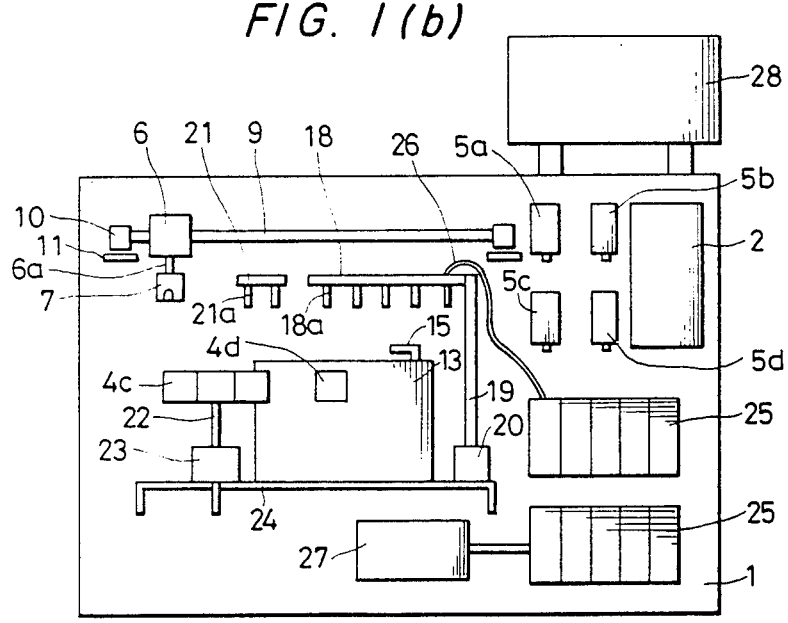
Figure 2:
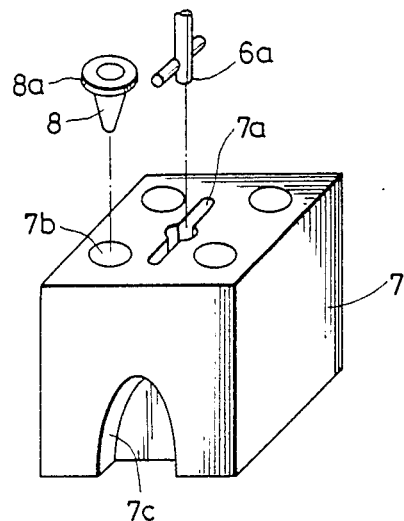
FIG. 2 is a perspective view of the head element and bucket assemblies.
Figure 3:
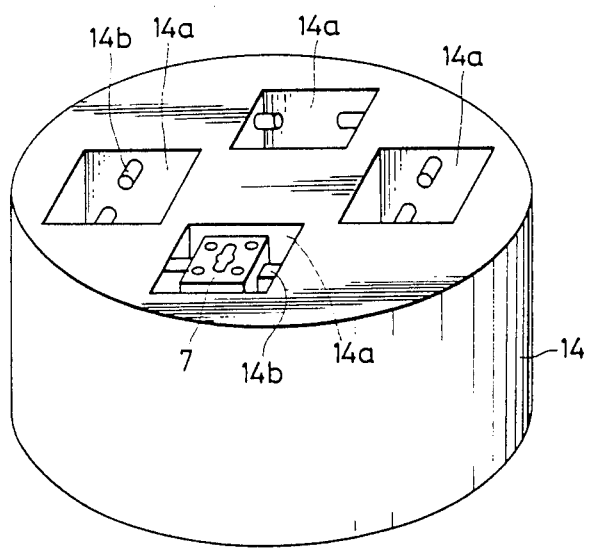
FIG. 3 is a perspective view of a rotor of a centrifugal separator.

FIG. 1 shows the whole construction of a preferred embodiment in accordance with the present invention. In FIG. 1, a reference numeral 1 designates a body frame, 2, 3 a temperature controller and a freezer, respectively, provided within the frame, and 4a–4d thermostat tanks. respectively, as thermostat devices, which are controlled to a constant temperature by the temperature controller 2 and the freezer 3, in which the thermostat tanks 4a, 4b, 4c and 4d are maintained at temperatures of $-40°$ C., $20°$ C., $90°$ C. and $4°$ C., respectively, by a refrigerant from the freezer 3 or by a heater. Reference numerals 5a to 5d designate liquid medium accommodators into which medium are supplied correspondingly to the thermostat tanks 4a to 4d, respectively, in which accommodators 5a, 5b and 5c, and 5d accommodate therein ethyl alcohol, ethylene glycol and water, respectively. A reference numeral 6 designates a manipulator for moving a bucket 7 in a three-dimensional fashion and has a head element 6a for hanging the bucket 7. The bucket 7 is in the form of a box as shown in FIG. 2 and has a key-hole shaped hole 7a into which an end of the head element 6a is inserted, a cylindrical hole 7b into which a reaction container 8 is accommodated, and an engaging notch 7c used when the bucket is inserted into a centrifugal separator described later. The manipulator 6 is movable in a direction of an X-axis (in a lateral direction of FIG. 1 (a)) along a guide rail 9, said guide rail 9 being movable in a direction of a Y-axis (in a vertical direction in FIG. 1 (a)) along a guide rail 11 through driving blocks 10 provided on both ends thereof, the manipulator 6, the guide rails 9, 11 and the block 10 constitute a transporting device for the container 8. The head element 6a is expandable in a direction of a Z-axis (in a vertical direction in FIG. 1 (b)) and is movable round the Z-axis. Accordingly, when the head element 6a is rotated after the former has been inserted into the hole 7a of the bucket shown in FIG. 2, the bucket 7 can be hung detachably. A reference numeral 12 designates a rack in which a plurality of buckets 7 may be accommodated, 13 a centrifugal separator provided substantially in the central portion of the apparatus, and 14 a rotor rotatably accommodated within the centrifugal separator 13. The rotor 14 is designed as shown in FIG. 3, and has a hole 14a for accommodating the bucket 7 therein and a pair of holding pins 14b projected oppositely from the inner wall of the hole 14a, the holding pins 14b being brought into enegagement with a notch 7c of the bucket whereby the bucket 7 may be held swingingly within the hole 14a. A reference numeral 15 designates a rotor position detecting sensor provided on the centrifugal separator 13 so as to be positioned above the rotor 14, 16 a rotation positioning motor for accurately positioning a rotational amount of the rotor 14, 17 a mixer accommodating therein the bucket 7 and driven to be agitaged by a driving portion not shown, and 18 a reagent supplying device having a plurality of nozzles 18a (including also suction nozzles for waste liquids), the supplying device 18 being driven in a direction of a Z-axis by means of a lifting driving beam 19 together with a nozzle 18a. A reference numeral 20 designates a motor driven to move the beam 19 up and down. A reference numeral 21 designates a dryer for drying the reaction container 8 within the bucket 7 and has a drying nozzle 21a. A reference numeral 22 designates a beam for moving the thermostat tank 4c in a direction of a Z-axis when necessary, and 23 a motor for driving the beam 22, the motor 23 as well as the aforementioned motor 20 being secured to the frame 1 through a base 24. A reference numeral 25 designates a plurality of distribution pumps provided corresponding to the reagent supplying nozzle 18a and the drying nozzle 21a, each supplying the reagent or air to each nozzle through a bendable pipe 26 (suctioning air for the suction nozzle) (only one pipe is shown but others are omitted). A reference numeral 27 designates a waste liquid portion for recovering the waste liquids from the thermostat tanks 4a–4d and from the suction nozzle out of the nozzle 18a, and 28 a controller comprising a microcomputor for controlling all the aforementioned manipulator 6, thermostat tanks, distribution pumps 25 and the like.

Figure 4A:
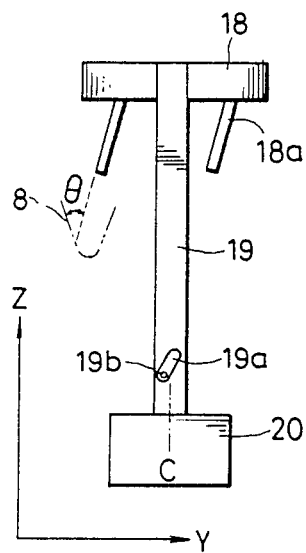
FIGS. 4 (a) and (b) illustrate the operation of upward and downward movements of a reagent supplying device.
Figure 4B:
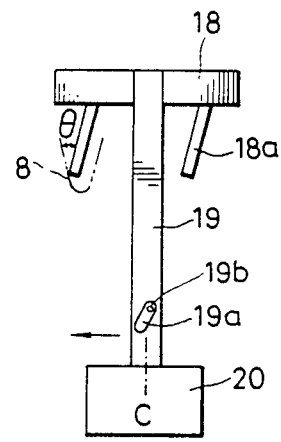

Next, the operation will be described. First, a plurality (four in the illustrated embodiment) of predetermined samples (such as DNA samples) are prepared, which are respectively put into the reaction containers 8 which are then accommodated into the bucket 7. Since the reaction container is formed with a flange 8a as shown in FIG. 2, it is positioned at the edge of the hole 7b of the bucket 7. At the same time, containers 8 containing therein another samples are respectively accommodated into other buckets 7, and the thus prepared buckets 7 are arranged plural in number are arranged on the rack 12. Next, when predetermined sequence data or the like are inputted into the controller 28 through a keyboard not shown, then required processing of samples will be completed in fully automated fashion. That is, as described above, the manipulator 6 drives the buckets 7 in the three-dimensional fashion and hangs the buckets within the rack 12 to move them while being positioned to the accommodators of the respective devices. In supplying the reagent by the reagent supplying device 18, the nozzle 18a is moved down along with the beam 19 by the motor 20 till it comes into contact with the inner wall surface of the reaction container 8. As shown in FIG. 4, the nozzle 18a is inclined in the direction of the Y-axis, and the beam 19 is formed with an inclined slot 19a parallel thereto which is in engagement with a pin 19b at a position fixed to the motor 20. Therefore, as the beam 19 moves down, the beam 19 is simultaneously driven also in the direction of the y-axis, and after all the nozzle 18a is moved down obliquely in a direction of an extension line thereof and comes to contact with the inner wall of the reaction container at an acute angle $\theta$. Generally, it is difficult to supply a fine amount of sample through the nozzle but in the illustrated embodiment, a supply of sample is made in direct contact with the inner wall surface of the reaction container 8 and therefore, shifting from the nozzle to the reaction container can be carried out in a stabilized manner. At this time, since the reaction container 8 along with the bucket 7 are accommodated within the thermostat tank 4d at a room temperature of 4° C. (the interior of apparatus is maintained at 4° C.), reaction heat may be absorbed when the reagent is supplied. It will be noted that in obliquely lifting the nozzle 18a, the beam 19 can be inclined parallel to the nozzle 18a and the beam can be driven in an axial direction as it is.

Where the reaction container 7 is accommodated within the centrifugal separator 13, since the rotor 14 is stopped at the rotated position of 90° unit by the sensor 15 and the rotation positioning motor 16, if the bucket 7 is moved by the manipulator 6 to a predetermined position, it may be accommodated into the hole 14a. The buckets 7 are accommodated within four holes 14a, and when the rotor 14 is rotated by means of a motor not shown, the buckets 7 are rotated round the engaging portions between the pair of notches 7c and holding pins 14b and become suitably balanced to assume an attitude stabilized with respect to the centrifugal force.

When the centrifugal separator 13 stops, the manipulator 6 again causes the reaction container 8 along with the bucket 7 to move and they are arranged at suitably predetermined accommodating positions of the mixer 17 or the thermostat tanks 4a, 4b, 4c or etc. in accordance with the procedure signal from the controller 28.

In drying the reaction container 8, a supernatant liquid is first discharged by the suction nozzle within the nozzle 18a and thereafter the bucket 7 is arranged below the dryer 21. At this time, if the thermostat tank 4c at 90° C. is moved up through the beam 22 so that it may be arranged in proximity of the nozzle 21a, the reaction container may be dried more rapidly.

The above-described processing is carried out in a time series manner with respect to the respective plural reaction containers 8 within the plurality of buckets 7. It is therefore desirable, though not shown in FIG. 1, that the thermostat tanks 4a to 4c has the same number (four) of accommodators of buckets 7 as that of the holes 14a provided in the centrifugal separator 14. Also for automatic operation, if more than eight bucket accommodators are provided on the rack 12, it is effective because two cycles of processing may be made.

If the provision is made wherein for example, a reflector or the like is secured onto the upper surface of the rotor 14 corresponding to the position of the sensor 15 so that the sensor 15 may effect photo-detection, the position of said reflector can be detected as an original point of rotation of the rotor 14. Thereafter, the rotor 14 is rotated through a suitable amount by the positioning motor 16 comprising a pulse motor or the like so that the hole 14a may be stopped at a predetermined position.

The temperature controller 2 is provided to always maintain the room temperature within the apparatus at 4° C. and to control, to a predetermined level, the temperatures of the liquid medium (ethyl alcohol, ethylene glycol) within the thermostat tank 4a cooled through the refrigerant from the freezer 3 and within the thermostat tanks 4b, 4c heated by a heater not shown. The temperature controller 2 is controlled by the data inputted into the controller 28.

Figure 5:
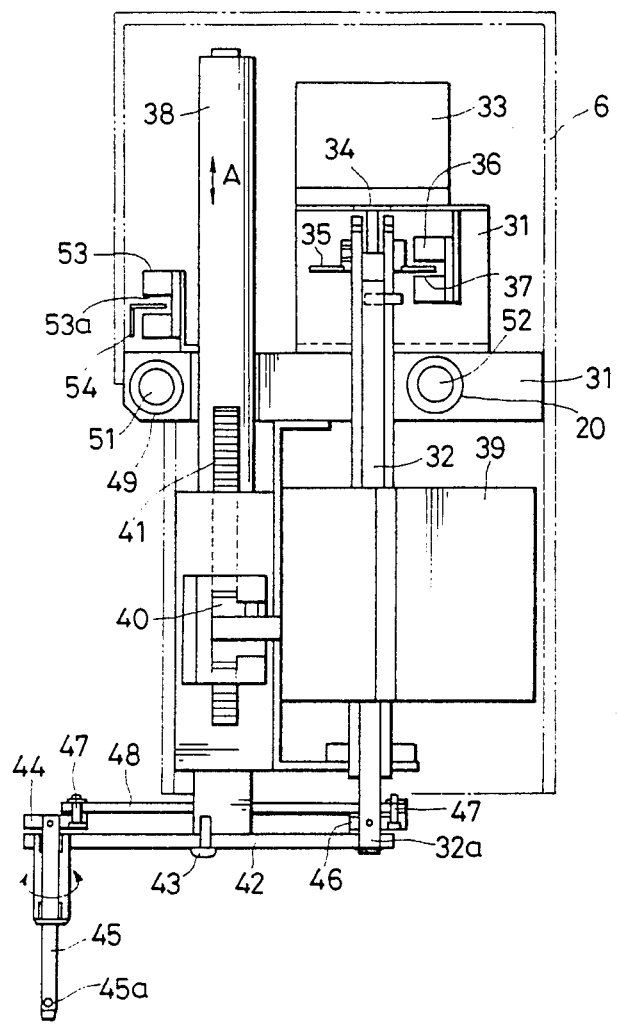
FIG. 5 is a structural view of a driving mechanism for a head element.
Figure 6:
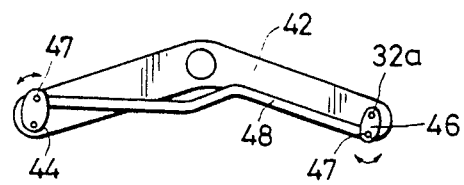
FIG. 6 is a fragmentary plan view of a rotating mechanism therefor.

Mechanisms for the transportation of the buckets 7 in the direction as indicated at z by the manipulator 6 and for connection with and separation from the buckets by the head elements 6a are shown in detail in FIGS. 5 and 6.

In FIG. 5, a reference numeral 31 designates a base of the manipulator 6, the base having a first support shaft rotatably mounted thereon, the first support shaft 32 being rotatably coupled to a shaft 34 of a first motor 33 mounted on the base 31.

A rotational plate 35 is mounted on the upper end of the first support shaft 32, and a circumferential edge of the rotational plate 35 is positioned within a detection recess 37 of a first electric detection element 36 mounted on the base 31. In the illustrated embodiment, the rotational plate 35 comprises a light-tightness plate and the first electric detection element 36 comprises a photo-switch element. Therefore, the rotated position of the rotational plate 35 is detected by the correspondence between a required opening (not shown) provided in the circumferential edge of the rotational plate 35 and the first electric detection element 36, to control the rotated position of the first support shaft 32.

On the base 31 is provided a second support shaft 38 at a position parallel to the first support shaft 32 and movably up and down in a direction as indicated by arrow A, and a driving gear 40 of a second motor 39 mounted on the base 31 meshes with a rack portion 41 of the second support shaft 38. At the lower end of the second support shaft 38, a support plate 42 in the shape of substantially as a whole is fixedly mounted by means of a bolt 43 in a direction perpendicularly to the length of the second support shaft 38. The support plate 42 has, at one end thereof, a head element 45 (corresponding to 6a of FIG. 1), which is secured to a first rotational plate, rotatably mounted, and has, at the other end, a lower end 32a of the first support shaft 32 rotatably extended therethrough, said lower end 32a having a second rotational plate secured thereto. A connecting rod 48 is swingingly connected to the first and second rotational plates 44 and 46 through a pin 47 spaced apart from the head element 45 and the lower end 32a of the support shaft, said rotational plates 44, 46 being connected by the connecting rod so that they may be simultaneously interlocked and rotated.

At the lower end of the head element 45 is provided a locking rod 45a in a direction orthogonal to the axial direction of the head element 45, and the first support shaft 32 is rotated whereby the head element 45 may be rotated through the connecting rod 48 and rotational plates 44, 46.

While, in FIG. 1, the manipulator 6 is shown to be driven in a direction of an x-axis by the single guide rail 9 for the sake of simplicity, it should be noted that a plurality of guide rods can be used for stabilized transportation and positioning.

The body 31 is formed in substantially the central portion thereof with a pair of guide holes 49, 50, into which are loosely fitted a pair of guide rods 51, 52 for moving the present apparatus in a direction as indicated by X. When the guide holes 49, 50 are slidably moved relative to the guide rods 51, 52, the base 31 is moved. Mounted on one end of the base 31 is a second electric detection element 53, which has a recess 53a into which is inserted a position control member 54 supported by the body frame.

The case where the head apparatus constructed as described above is operated will be described. First, when the second motor 39 is rotated, it assumes the state that the second support shaft 38 is moved downwardly from the position shown in FIG. 5 and the head element 45 is inserted at the established height and into the locking hole 7a of the bucket 7 shown in FIG. 2. Subsequently, when the second motor 33 is rotated, the first support shaft 32 rotates to rotate the head element 15, in a direction as indicated by the arrow, provided on the support plate 42 through the connecting rod 48, and when the head element 45 inserted into the locking hole 7a, it is placed in engagement with the locking hole by the locking rod 45a. Next, the second support shaft 38 is driven upwardly by the second motor 39 whereby the bucket 7 may be raised by the head element 45. Thus, for example, when the manipulator 6 is slidably moved on the guide rod 51 under the raised condition, the head element 45 may be moved to another location.

For mixing of a small quantity of samples, it is general to give vibrations to the reaction containers to mix them but in case of using the automatic manipulator, the rest position thereof is necessary to be always constant. FIGS. 7 and 8 show the detail of the mixer 17 for that purpose, in which a reference numeral 61 designates a base bed which is the body of the mixer, 62, 63 a positioning motor and a rotating and driving motor, respectively, supported on the base bed 61, 64 an electromagnetic clutch for detachably switching a rotational shaft 62a of the positioning motor 62, 65 a driving shaft driven by the motor 62 through a clutch 64, and 66 a belt extended over a pulley 65a integral with the rotatary shaft, the belt 66 having the other end extended over a pulley 63b integral with a rotational shaft 63a of the rotating and driving motor 63. A reference numeral 67 designates an eccentric shaft fitted integral with the driving shaft 65, and a position display plate 68 showing an original position is provided at the end of a balancing projection 67a. A reference numeral 69 designates a swinging base plate pivotally supported on the eccentric shaft 67 through a bearing 70 and being vertically supported sandwiching a bearing 70 through a bearing support member 69a integral with the base plate 69 and a ring-like spacer 71. A reference numeral 72 designates a rubber-like resilient member one end of which is secured to the base bed 61, the other end thereof being secured to a corner portion of the swinging base plate 69 to swingingly support the base plate 69 relative to the base bed 61. A reference numeral 73 designates a column projected integral with the swinging base plate 69, and 74 a box-like swinging case locked at screw 75 to the column 73 and secured integral with the base plate 69, the case being formed with an opening 74a for accommodating therein the bucket 7, which will be described later. A reference 76 designates a support block secured to the upper surface of the swinging case 74 and has pins 76a for supporting the bucket 7 provided so as to be opposed through the openings 74a. A reference numeral 77 designates a position detector provided on the base bed 61 so as to correspond to the positon display plate 68 and is a known device which comprises a light emitting element and a light receiving element.

When the bucket 7 along with the reaction container 8 are mounted on the opening portion 74a of the mixer device by the manipulator 6, the shaft 62a of the positioning motor 62 is not connected to the driving shaft 65 since the clutch 64 is normally open, and the driving shaft 65 is rotated at a high speed by the rotating and driving motor 63 through the belt 66. At this time, the eccentric shaft 67 is rotated integral with the driving shaft 65 but is swingingly rotated in accordance with the eccentric amount relative to the driving shaft 65. This swinging rotational motion is transmitted to the swinging base plate 69 through the support portion 69a while being slidably moved within the bearing 70. The swinging base plate 69 is supported at four corners thereof by the resilient members 72 and effects its swinging motion without being rotated to swing the swinging case 74 secured through the column 73. Accordingly, the sample and reagent within the reaction container 8 accommodated within the bucket 7 mounted in the opening 74a are fully agitated.

After agitating has been completed and the motor 63 stops. the driving shaft 65 stops at a suitable position, the swinging case 74 is also stopped at a suitable position. Since the chemical analyzer of the present invention is the apparatus which uses the manipulator 6 to effect fully automated sequence, the hole 7a of the bucket 7 has to be present at a position inputted into a control section (not shown).

Then, the electromagnetic clutch 64 is closed, and the shaft 62a of the positioning motor is connected to the driving shaft 65. The motor 62 is rotated at a low speed and stops when the eccentric shaft position detector 77 detects the display plate 68 for displaying the positon of the original point. Accordingly, the swinging case 74 stops at the position of the original point without fail within one full rotation of the driving shaft 65. When the positioning operation has been completed, the clutch 74 is open and is returned again to a state wherein the next swinging motion is possible to make.

While in the above-described embodiments, an optical sensor and a display plate have been used as position detector means for the eccentric shaft 67, it should be noted that a rotational decoder can be disposed between the positioning motor shaft and the driving shaft and the motor can be stopped by the output of the decoder.

What is claimed is:

1. A chemical manipulator comprising, in a housing, a centrifugal separator capable of accommodating at least more than one reaction container, a mixer device thermostatic device, a dryer for drying said reaction containers, a reagent supplying device for supplying a reagent to said reaction containers, a transporting device located in an upper portion of said housing having means for moving said reaction containers in a three-dimensional fashion, including guide rails in the X-direction and the Y-direction at a right angle thereto, for movement of said container in said upper portion of said housing and conveying said containers while being located relative to said centrifugal separator, said mixer device, said thermostatic device, said dryer and said reagent supplying device, and a controller for controlling said centrifugal separator, said mixer device, said thermostatic device, said dryer, said reagent supplying device and said transporting device, wherein said mixer device comprises an eccentric shaft supported on a base bed and a first motor for rotatably driving said eccentric shaft, a swinging base plate swingingly supported on said base bed through a resilient member and pivotally supported on said eccentric shaft, a swinging case provided integral with said swinging base plate, a reaction container accommodating portion formed on said swinging case, a position detecting means for detecting a rotated position of said eccentric shaft, and a second motor for rotatably driving said eccentric shaft to a predetermined position in accordance with a signal of said detection means, characterized in that when said first motor stops, said swinging case is rested at a predetermined position by said second motor.

2. A chemical manipulator comprising, in a housing, a centrifugal separator capable of accommodating at least more than one reaction container, a mixer device, thermostatic device, a dryer for drying said reaction containers, a reagent supplying device for supplying a reagent to said reaction containers, a transporting device located in an upper portion of said housing having means for moving said reaction containers in a three-dimensional fashion, including guide rails in the X-direction and the Y-direction at a right angle thereto, for movement of said containers therealong in said upper portion of said housing and conveying said containers while being located relative to said centrifugal separator, said mixer device, said thermostatic device, said dryer and said reagent supplying device; and a controller for controlling said centrifugal separator, said mixer device, said thermostatic device, said dryer, said reagent supplying device and said transporting device, wherein said transporting device comprises a first support shaft rotatably provided on a base having a pair of guide portions for guiding a pair of guide rods movable in a bi-direction, a first motor provided on said base to rotate said first support shaft, a rotational plate formed on one end of said first support shaft, a first electric detecting element provided on said base to electrically cooperate with said rotational plate, a second support shaft provided movably up and down in a direction parallel to said first support shaft in said base, a rack portion formed on said second support shaft, a second motor provided on said base and having a driving gear which meshes with the teeth thereof to move said second support shaft up and down, a support plate provided fixedly in a direction orthogonal to the length of said support shaft at the lower end of said second support shaft, a first and second rotational plates rotatably provided on both ends of said support plate, a connecting rod provided between said first rotational plate and said second rotational plate to connect said both rotational plates, and a head element rotatably provided on one end of said support plate, said head element being formed integral with said second rotational plate and having a locking rod at the lower end thereof, characterized in that said first support shaft and said first rotational plate are connected integrally whereby said head element is rotated in association with the rotation of said first support shaft, and said second support shaft is moved up and down whereby said head element is moved up and down.

* * * * *